United States Patent [19]

Schneider et al.

[11] Patent Number: 5,074,861
[45] Date of Patent: Dec. 24, 1991

[54] MEDICAL LASER DEVICE AND METHOD

[76] Inventors: Richard T. Schneider, 17 Alachua Highland, Alachua, Fla. 32615; Richard H. Keates, 573 S. Sixth St., Columbus, Ohio 43206

[21] Appl. No.: 539,383

[22] Filed: Jun. 15, 1990

Related U.S. Application Data

[63] Continuation of Ser. No. 197,699, May 23, 1988, abandoned.

[51] Int. Cl.⁵ .............................................. A61B 17/36
[52] U.S. Cl. ......................................... 606/17; 606/3; 600/2
[58] Field of Search ................. 128/303, 1, 395–398; 219/121.6, 121.74, 121.75; 372/108, 70, 72, 79; 606/3, 4, 6, 15–17; 600/2

[56] References Cited

U.S. PATENT DOCUMENTS

| | | | |
|---|---|---|---|
| 3,304,403 | 2/1967 | Harper | 219/121 |
| 3,356,966 | 12/1967 | Miller | 372/72 |
| 3,392,261 | 7/1968 | Schollhammer | 372/72 |
| 3,404,350 | 10/1968 | Muncheryan | 331/94.5 |
| 3,471,215 | 10/1969 | Snitzer | 350/96 |
| 3,481,340 | 12/1969 | McKnight et al. | 128/395 |
| 3,622,743 | 11/1971 | Muncheryan | 128/303.1 |
| 4,120,293 | 10/1978 | Muckerheide | 128/665 |
| 4,237,364 | 12/1980 | Lemelson | 219/121 |
| 4,383,318 | 5/1983 | Barry et al. | 372/6 |
| 4,559,942 | 12/1985 | Eisenberg | 128/303 |
| 4,564,011 | 1/1986 | Goldman | 128/303.1 |
| 4,622,967 | 11/1986 | Schachan | 128/303.15 |
| 4,658,817 | 4/1987 | Hardy | 128/395 |
| 4,676,242 | 6/1987 | Doi | 128/303.1 |
| 4,682,335 | 7/1987 | Hughes | 372/6 |
| 4,729,373 | 3/1988 | Peyman | 128/303.1 |
| 4,757,515 | 7/1988 | Hughes | 128/396 |

FOREIGN PATENT DOCUMENTS

| | | | |
|---|---|---|---|
| 0105706 | 4/1984 | European Pat. Off. | |
| 3540763 | 5/1987 | Fed. Rep. of Germany . | |
| 2594686 | 8/1987 | France . | |
| 259961 | 12/1987 | France . | |
| 8702884 | 5/1987 | PCT Int'l Appl. | 128/303.1 |
| 8705794 | 10/1987 | PCT Int'l Appl. . | |
| 1554823 | 10/1979 | United Kingdom . | |

Primary Examiner—William E. Kamm
Assistant Examiner—Scott M. Getzow
Attorney, Agent, or Firm—Merchant, Gould, Smith, Edell, Welter & Schmidt

[57] ABSTRACT

An apparatus and method for conducting laser emulsification surgery are disclosed. Laser energy is generated within the hand held member (10) and is transmitted to the probe cylinder (15) at the distal end of the device (2). The apparatus is a hand held device which contains a laser light source and flashlamp (12) for generating and emitting the laser radiation. Preferably, an Erbium YAG laser is utilized. A light horn arrangement (18) or mirror arrangement (51) transmits the light energy from the source (12) to the proximal end of a probe extension member (15). The distal tip (31) of the probe extension member (15) is directed to the cataract or other target to be emulsified.

27 Claims, 4 Drawing Sheets

MEDICAL LASER DEVICE AND METHOD

This is a continuation, of application Ser. No. 07/797,699, filed May 23, 1988, now abandoned.

FIELD OF THE INVENTION

The present invention relates to laser surgery, and in particular to surgical operations on the eye. Specifically, the present invention relates to a method and apparatus for the emulsification and removal of cataracts, or similar surgical procedures.

BACKGROUND OF THE INVENTION

A cataract is a development of an opaque or clouded region in the crystal lens of the eye. Generally, the deterioration process is not reversible. The typical current treatment is to remove the cataract material completely. After the surgery, artificial lenses are provided to facilitate vision. Such lenses may be of a variety of types, including extraocular eye frames and lenses, extraocular contacts, and intraocular contact lens devices.

Recently, various microsurgery techniques have been developed to enable easier removal of the cataracts. One frequently used method is phaeco-emulsification. For application of this process, a small incision is made in the eye, and a probe, generally a titanium needle, is inserted therethrough. The probe includes a tip which vibrates in the ultrasonic region, on the order of 20,000 times per second. Such a probe is brought into direct contact with the lens, and the vibrations are used to break up, or emulsify, the lens material. This lens material or cataract debris is then withdrawn from the eye through means of suction devices or the like. Fluid flushing means is provided adjacent the needle for the inflow of fluid into the eye in order to prevent collapse of the eye and to cool the vibrating needle and the area in contact with it.

This method suffers from a number of disadvantages. First, the nucleus may fragment, causing corneal damage, or the nucleus may be too hard to emulsify. The probe generates substantial risk of significant damage in various portions of the eye, if inadvertently brought into contact therewith, causing many surgeons to be reluctant to utilize the phaeco-emulsification technique. Second, rupture of the posterior capsule can occur easily with ultrasonic devices. Third, a great deal of manual dexterity and skill on the part of the surgeon are required to properly perform the operation. Fourth, a large amount of irrigation, or fluid exchange, is required in the anterior segment, greatly increasing the chances of corneal damage. And fifth, the likelihood of iris injury is high. As a result, while phaeco-emulsification does offer many advantages over former surgical methods, it is still not fully accepted, nor is it completely advantageous.

Conventional laser tools have been utilized in the past in surgical applications, but they have required remote energy sources. Typically, a relatively high power laser source communicates with the hand held tool by means of an articulated arm arrangement or the like. Unfortunately, this arrangement can be awkward for surgical applications and results in a loss of considerable laser energy during transmission of light to the hand piece.

What has been needed has been a method for cataract removal which does not involve a vibrating probe or an articulated arm arrangement, and which is substantially free of the inconveniences and problems associated with these methods, but which otherwise utilizes the advantages of a microsurgery technique. Further, what has been needed has been an apparatus for application of the needed method.

OBJECTS OF THE INVENTION

Therefore, the objects of the present invention are: to provide an apparatus for advantageous removal of cataract, or lens material from the eye; to provide such an apparatus where laser surgery is applied to accomplish emulsification of the cataract; to provide a preferred such apparatus which utilizes light of a wavelength generally not posing substantial unacceptable risk of damage to the eye; to provide a surgical device in which a probe capable of transmitting a laser emission is mounted on a hand held tool to facilitate manipulation of the probe; to provide a hand held surgical tool in which laser light is generated within the hand piece to minimize transmission distance and energy loss; to provide such a device wherein an extension cylinder mounted upon the probe is readily removable and replaceable; to provide such a device including a suction means for removal of emulsified lens material; to provide such a tool including means for transmitting fluid to a site of emulsification in order to fill the volume vacated following emulsification and/or to rinse the area; to provide means for transmission of light from a laser to a the probe extension cylinder in such a device, whereby light of a wavelength substantially absorbable by water and/or carbon dioxide can be efficiently transmitted to the extension cylinder for use; to provide such an arrangement which is particularly well-adapted for utilization in association with laser light having a wavelength of about 2.94 micrometers; to provide an arrangement which is particularly well-adapted for use in association with light generated by an erbium laser; to provide an arrangement in which laser light is efficiently generated and transmitted through the hand piece and onto the extension cylinder of the probe; to provide an efficient means of concentrating a combination of several laser outputs onto the extension cylinder mounted upon the probe; to provide a hand held surgical tool which is easily manipulated but which does not require a remote laser light source and complex transmission mechanism; to provide means for cooling the laser generation system; to provide a device which delivers the laser radiation directly to the cataract or other target being treated; to provide a device which minimizes laser light loss due to transmission and thereby requires a minimum amount of power; to provide an apparatus according to the invention which is particularly well-adapted for application of the method proposed; and to provide such an apparatus which is relatively inexpensive and easy to produce, assemble and use, and which is particularly welladapted for the proposed usages thereof.

It is a further object of the present invention to provide an arrangement and method well suited for adaptation as fiberoptic and laser technology changes.

It is another object of the present invention to provide a method utilizing a laser apparatus for ophthalmic and other delicate surgery, particularly retinal or vitreous surgery, which requires relatively little energy, which is compact and easily manipulable and which does not suffer from the disadvantages of the prior art devices.

Another object of the invention is to provide a means for intensifying the laser radiation by concentrating it to a thin beam prior to emergence of the laser radiation from the hand-held laser device.

Other objects and advantages of the present invention will become apparent from the following description, taken in conjunction with the drawings, wherein preferred embodiments of the present invention is set forth by way of illustration and example.

SUMMARY OF THE INVENTION

The present invention concerns an apparatus for utilization in association with laser surgery to emulsify cataract material in the eye. The apparatus is a hand held device which contains a laser light source for emitting the laser light, the source including a central, longitudinal flashlamp. Light such as that generated by erbium YAG lasers is preferred, having a wavelength of 2.94 micrometers. After generation and emission of the laser light within the hand held member, a transmission means is provided to direct the light energy from the source to the proximal end of a probe extension member. The distal tip of the probe extension member is directed to the cataract or other target to be emulsified. Various configurations of the laser emission means are disclosed, including a single laser rod surrounded by a flashlamp, and a flashlamp surrounded by a plurality of laser rods. Also, several embodiments of the transmission means are disclosed, including a bent light horn, a straight light horn, a lens arrangement, and a mirror arrangement.

Laser probes and laser surgery are well-known. Generally, problems have related to transmission of the necessary light from the light source or laser to a remote region, in this instance the eye, for surgical operation.

According to the present invention, a method and apparatus are provided whereby the above-described problems are addressed. Specifically, a laser emulsification apparatus is provided for use in optical surgery. The invention comprises a hand held tool utilizable by the surgeon to manipulate a probe into the immediate vicinity of the cataract. With the medical tool of the present invention, the laser source is located within the hand piece itself. In this manner, the laser radiation is generated in close proximity to the eye, so that relatively little laser light is lost during transmission.

In a preferred embodiment, a removable and replaceable extension cylinder is mounted within a probe extension. The preferred probe extension cylinder includes a mounting and release mechanism to facilitate removal and replacement of the extension member, as needed for example to facilitate a sterilization process.

Preferably, the device has two fluid communication systems. A first of these is a chamber which provides a means for applying a suction, or fluid draw, from the immediate vicinity of emulsification. Through use of this vacuum or suction system, emulsified material can be readily withdrawn from the vicinity of the probe tip, without removal of the probe from the eye chamber and in some instances concurrently with emulsification.

A second fluid flow system in the device provides a system for transmission of fluid or the like into the region wherefrom the emulsified lens is removed. This transmission system can provide for a cleansing wash of the area. Further, this fluid transmission system can provide a fluid such as a saline solution to fill any void created by destruction of the lens.

As previously suggested, the preferred device according to the present invention is particularly well suited for utilization in association with erbium lasers which generate light having a wavelength on the order of about 2.94 micrometers. Light of such a wavelength is generally desirable for use in association with laser emulsification surgery since large effects can be achieved at relatively low energy levels. This wavelength is readily absorbed by materials in the body such as water and hydrocarbons. Due to the large absorption band of water at this wavelength, no formation of sticky material on the probe tip takes place, which is a serious problem with other wavelengths. Also, for the same reason, this light will be absorbed by body tissue before it is transmitted a sufficient distance to cause significant damage to tissue not in the immediate vicinity of the probe tip, for example, damage to portions of the eye other than those which are intended to be emulsified.

The present invention includes several embodiments of means for generating and transmitting laser radiation. The generation and transmission means are designed to be highly efficient, so as to minimize undesirable absorption and laser light loss. This also results in a reduction in the power required.

The medical device of the present invention is also advantageous in that it is highly portable and, thus, easy to manipulate by the surgeon. The laser light is generated within the hand held device, so that a complex light transmission mechanisms are not required. The design of the generation and transmission means provides for advantageous miniaturization of the hand held device. The laser energy is not transported through a significant distance, so that absorption and energy losses are minimized.

The drawings constitute a part of the specification and include exemplary embodiments of the invention while illustrating various objects and features thereof. It will be understood that in some instances relative material thicknesses, and relative component sizes, are shown exaggerated to facilitate an understanding of the invention.

DETAILED DESCRIPTION OF THE PREFERRED EMBODIMENTS

As required, detailed embodiments of the present invention are disclosed herein. However, it is to be understood that the disclosed embodiments are merely exemplary of the invention, which may be embodied in various forms. Therefore, specific structural and functional details disclosed herein are not to be interpreted as limiting, but rather as the basis for the claims and as a representative basis for teaching one skilled in the art to employ the present invention in virtually any appropriately detailed system.

Referring to the Drawings, the hand held laser tool of the present invention is shown generally at 2. The tool 2 includes a handle member 10 and a partially tapered probe extension member 11 mounted on one end of the handle member 10. During use of the device 2, a small cylindrical portion of the probe extension 11 is inserted into the eye, and brought into alignment with the cataract material or other target to be emulsified and removed. Laser radiation is transmitted longitudinally through the probe extension 11, and is directed at the cataract or target to be emulsified. The probe extension 11 includes means, as described below, to provide for withdrawal of emulsified cataract material. Further, the probe extension 11 includes means described below which provide for direction of fluid into the cavity from which the emulsified lens material has been removed.

The handle member 10 is sized and configured to fit completely and comfortably within a hand. It will be understood that the handle 10 may be formed from a variety of materials, including plastics, and may be designed in a variety of shapes. Generally, it will be preferred that a convenient shape for gripping, such as a cylindrical shape, be provided.

The probe extension 11 juts outwardly from handle 2, and carries an extension cylinder or probe 15 at its tip. Preferably the probe 15 is a blunt, thin cylinder that can be used to transmit a sufficient amount of light energy to the cataract to break it up due to emulsification occurring as a result of breaking the O—H bands of the large organic molecules. The preferred cylinder 15 is solid and elongate having a generally circular cross-section preferably on the order of about one millimeter or smaller in diameter. It should be noted that the tip 31 of the cylinder 15 can be of a variety of shapes, sizes or configurations depending upon the particular application. The end of the probe extension 11 is inserted through a relatively small incision in the eye, and can be maneuvered very close to the cataract to be emulsified, so that the tip 31 of the cylinder 15 may come into contact with the individual cataracts.

The cylinder 15 of the hand piece is, in the preferred embodiment, made of calcium fluoride. The cylinder 15 can also be made of magnesium fluoride, zinc sulfide, zinc selenide, magnesium oxide, or cadmium telluride. These types of materials show a small but measurable absorption for the laser wavelengths quoted. However, the short distance in which the radiation is carried by the delivery cylinder 15 makes this negligible. Further, other materials, including ones that can be drawn into optical fibers and materials which may eventually be developed, may be utilized for the cylinder 15.

In the preferred embodiment, the cylinder 15 is removable and replaceable after wear or for sterilization purposes. Preferably, cylinder 15 is removably mounted within the extension member 11 by means of a mounting and release mechanism. The mounting and release mechanism operates by means of frictional contact with apertures in one or two bushings or O-rings 18. The cylinder 15 thus can be removed simply by pulling it outwardly from the bushing 18. Insertion of the cylinder 15 may be accomplished in a reverse manner. As a result, the cylinder 15 can be readily removed for purposes of sterilization and/or disposal.

In operation, probe extension 11 is inserted into an eye, in a manner bringing the tip 31 of the cylinder 15 into the immediate vicinity of the cataract material to be emulsified. Through means described below, light is transmitted to and through the cylinder 15, and the cataract material is emulsified.

A preferred form of the probe 15 includes a reflective layer 48 on its cylindrical wall. The reflective layer 48 is formed from a reflective material such as gold, silver, or the like, coated onto the cylinder 15. This material will tend to reflect light directed thereagainst, so that all of the laser energy is prevented from being emitted outwardly from the cylinder 15 and is restricted to being emitted from the tip 31 of the cylinder. Portions of the eye which are particularly sensitive to damage from laser surgery are blocked from the laser light. Thus, emulsification can be effected relatively safely, even in particularly sensitive areas of the eye.

The four embodiments described herein utilize the same general principles to generate or emit laser light within a hand held device and to transmit the laser light from the source to the surgical target to be emulsified. However, various generation and transmission means are utilized in the different embodiments.

The laser source and generation means are generally the same for the first three embodiments, illustrated in FIGS. 1-9. In these embodiments, the pump for the laser light source is a high pressure flashtube 12 or a similar suitable light source which is located longitudinally in the center of the hand piece 10. The flashtube 12 produces very brief, intense flashes of light, there being approximately 10 to 100 pulses per second. In the preferred embodiment, a laser having a wavelength in the range of approximately 2.9 to 3.1 micrometers is utilized, such as an erbium YAG (yitrium aluminum garnet) laser having a wavelength of 2.94 micrometers.

The flashlamp 12 is surrounded by a number of thin, parallel Er-YAG rods. In the preferred embodiment, the central flashtube 12 is approximately five millimeters in diameter. Preferably, the laser rods 13 are approximately one to four millimeters in diameter. In the embodiment illustrated in the cross-sectional view of FIG. 7, there are eight rods 13, each rod being approximately 2.2 millimeters in diameter. Preferably, the multiple rods 13 are mounted very closely to the central flashtube 12, so that the rods almost touch the flashtube 12. There is only a small gap between the individual adjacent rods 13. As a result, a great percentage of the light flux emitted by the lamp 12 will be intercepted by the rods 13.

Figures 3, 7, 8:
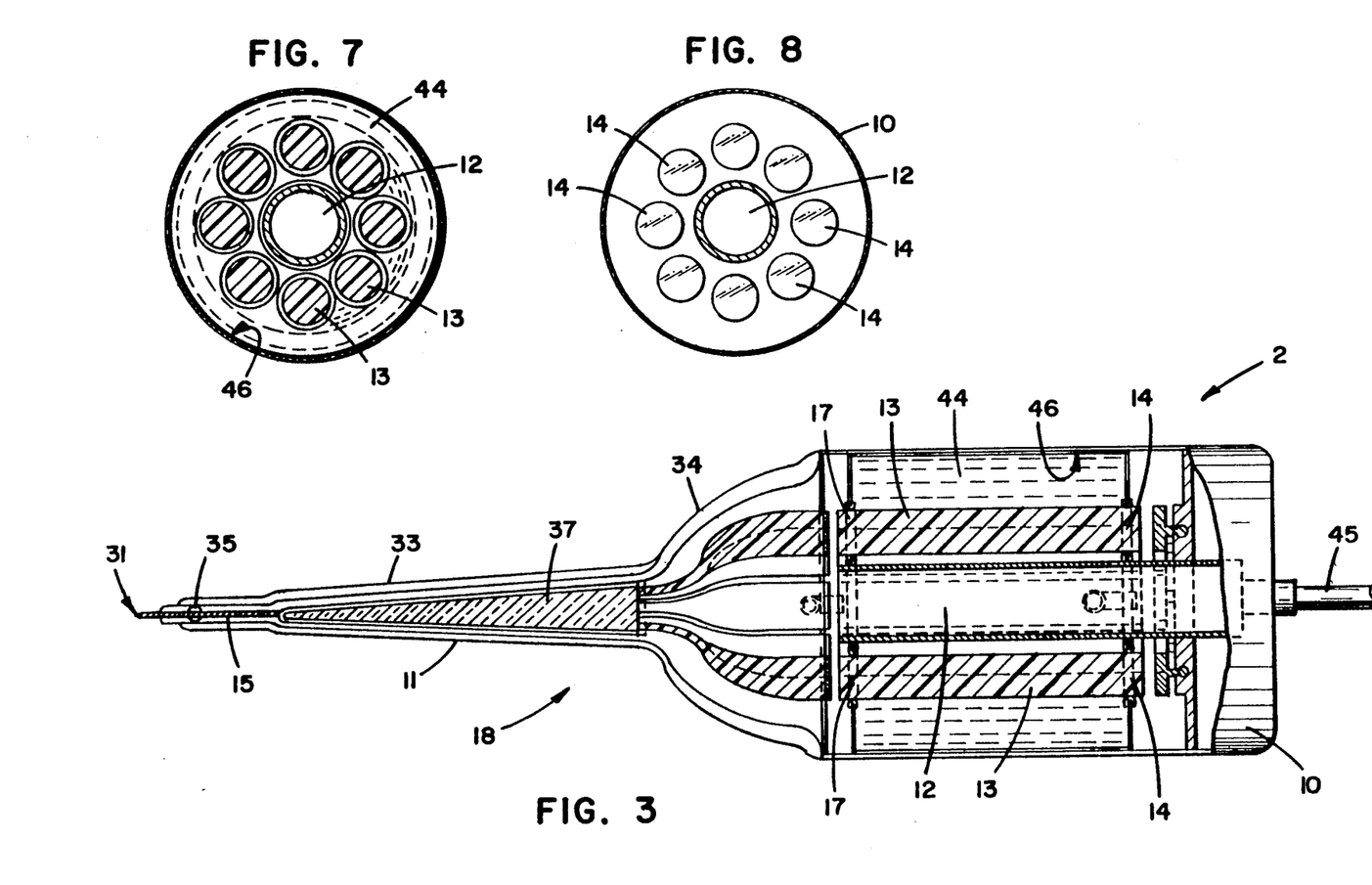
FIG. 3 is a cross-sectional view taken along line 3—3 of FIG. 2 of the first embodiment of the device of the present invention.
FIG. 7 is a cross-sectional view, taken along lines 7—7 of FIGS. 2, 5 and 6, of the flashtube and laser rods of the first, second and third embodiments of the device of the present invention.
FIG. 8 is a cross-sectional view, taken along lines 8—8 of FIGS. 2, 5 and 6, of the light rod arrangement of the first, second and third embodiments of the device of the present invention.

By using a multitude of thin rods 13 as compared to using a single thick rod, the surface-to-volume ratio is larger for a given rod volume, the volume determining the number of atoms capable of populating the upper laser level. This increase of surface-to-volume ratio provides for better cooling of the rods.

The inner surface 46 of the housing 10 is preferably a cylindrical mirror which serves to reflect and return any light which passes between the rods 13 or completely penetrates a rod 13. Reflection of the light by the cylindrical mirror returns the light back toward the flashtube 12. This results in an efficient coupling between the light source 12 and the laser rods 13. Thus, essentially all light generated in the flashtube 12 is absorbed by the laser rods 13.

A particular problem to the utilization of laser emulsification methods for cataract surgery involves the transmission of light of appropriate energy or wavelength to the site of emulsification. As discussed above in the preferred embodiment, light having a wavelength of approximately 2.9 to 3.1 microns is utilized with the device 2 of the present invention. Light of this wavelength is of low energy and is of a wavelength readily absorbed by materials found in the body, such as hydrocarbons and water. Thus, the laser radiation is substantially dissipated, in part through absorption by bodily fluids, before it can be transmitted a sufficient distance to cause much damage to more remote optical tissue regions. Erbium lasers are particularly desirable, as they generate light of about 2.94 microns.

Each rod 13 has an input mirror 14 and output mirror 17 at its two ends. The input mirrors 14 at the proximal end of the rods 13 provide for 100% reflection of light back into the rods 13. The mirrors 14 are illustrated in FIG. 8. At the remote end of the rods 13, output mirrors 17 are positioned. These mirrors 17 provide for less than 100% reflection. Thus, while most of the light energy directed toward the output mirrors 17 of the rods 13 is reflected back into the rods 13, intensifying the beams, some of the waves of energy pass through the output mirrors 17 and into the transmission system for gathering the light and directing it toward the probe cylinder 15. The mirrors 14 have the proper radius of curvature to form a stable cavity, and are individually adjustable in the preferred embodiment. A reflective coating on the end of the laser rods 13 may be used to supplement and/or replace the mirrors 17, 14.

The mirrors 17, 14 on either end of the rods 13 form a resonator. Radiation that is directed straight along the axis of the rods 13 bounces back and forth between the mirrors 17, 14 and builds a strong oscillation. Radiation is coupled out by making one rod mirror 17 partially transparent so that part of the amplified light can emerge through it. Thus, one mirror 14 is a reflecting end plate, whereas the other mirror 17 is partially transparent.

The laser rods 13 are supported within the housing 10 by any of the well-known means. In operation, sufficient power is supplied to the flashlamp 12 to cause the laser rods 13 to fire. An electric cable 45 extends from one end of the housing 10 to an external power supply source (not shown). When the flashlamp 12 is energized, its high-intensity light radiates in all directions in the chamber. The radiation strikes the housing mirror which, in turn, reflects the light onto the rods 13. A laser beam from the rods 13 is reflected by the mirrors 17, 14 and, in turn, is reflected through the front end of the rods 13, and carried by the transmission means to the probe extension 11 and cylinder 15.

To prevent excess heating of the laser element, cooling means is provided. A water jacket 44 surrounds each rod 13 for cooling. The rods 13 are cooled by suitable liquid, which is pumped through the hand piece 10 by an external pump (not shown). An input conduit 39 and output conduit 40 are used to transmit the coolant, which may be water, air, or other suitable fluid. The liquid coolant, e.g., distilled water, will absorb only a few percent of the emitted light because of the small distance between the adjacent rods 13. Each end of the laser rods 13 is preferably sealed with a O-ring 47 to keep the liquid coolant from reaching the laser mirrors 14, 17. Other elements, such as fins or a thermometer, may be used in conjunction with the cooling means described.

The transmission means serves to gather the light from the laser rods 13 and direct the light toward the probe cylinder 15. The transmission means varies according to the different embodiments. In the first embodiment illustrated in FIGS. 2-3, a light horn system 18 is provided. The light horn system 18 is a preferably funnel-shaped device made of a high refractive index material, so that light, once inside, will undergo total reflection on the walls and thereby stay inside the light horn 18 while being concentrated.

Figures 1, 2, 4, 9:
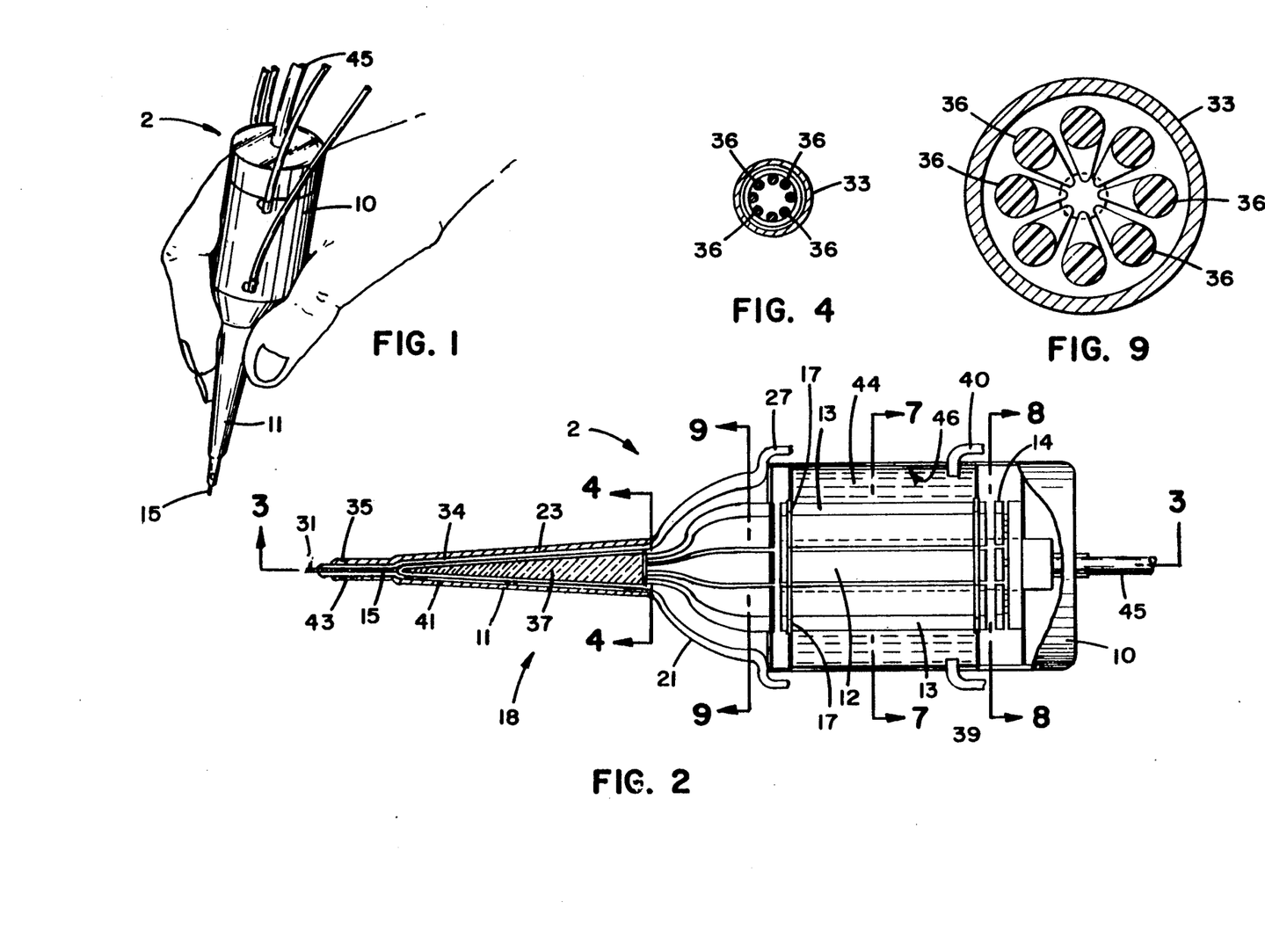
FIG. 1 is a perspective view of the medical laser device of the present invention.
FIG. 2 is a side elevational view, in section, of the first embodiment of the device of the present invention.
FIG. 4 is a cross-sectional view, taken along line 4—4 of FIG. 2, of the light horn of the first embodiment of the device.
FIG. 9 is a cross-sectional view, taken along lines 9—9 of FIGS. 2 and 6, of the bent light horn of the first and third embodiments of the present invention.

The light horn 18 includes two general sections indicated at 33 and 34. As illustrated in FIGS. 2 and 3, section 33 comprises a plurality of individual, conical shaped horns 36 having a bent or curved configuration. Each horn 36 collects light from an associated rod 13, and directs it into the second light horn system 34. The light horns 36 taper from the relatively large size illustrated in FIG. 9 to the relatively small diameter illustrated in FIG. 4, thereby concentrating the laser energy.

The input end of each light horn 36 is preferably flat and coated with a suitable reflecting layer. The light horn arrangement 18 serves to shift the rays parallel to their direction of propagation without taking up an undue amount of space.

An optical material such as those quoted above may be used to form the light horns 36. There are mathematical equations to calculate the appropriate bend or tapering angles for each horn. In this manner, the aspect ratios and lengths can be calculated by those skilled in the art to provide for efficient concentration of the laser radiation.

The output of the light horn 33 illuminates the input part of the other, more slender light horn 34, which, in turn, illuminates the cylinder 15. The second light horn system 34 proximate the probe extension member 11 comprises a single straight cone 37, which receives light energy from each of the individual horns 36. The cone 37 tapers until it focuses laser light into a narrow beam directed at the removable cylinder 15.

The cylinder 15 is illuminated by the slender light horn 37 which does not need to be flexible. The light horn 37 may be made of various materials, including fused silica, and also calcium fluoride, and other suitable IR materials such as potassium chloride (KCl), lithium fluoride (LiF), potassium bromide (KBr), and sodium chloride (NaCl).

Figure 6:
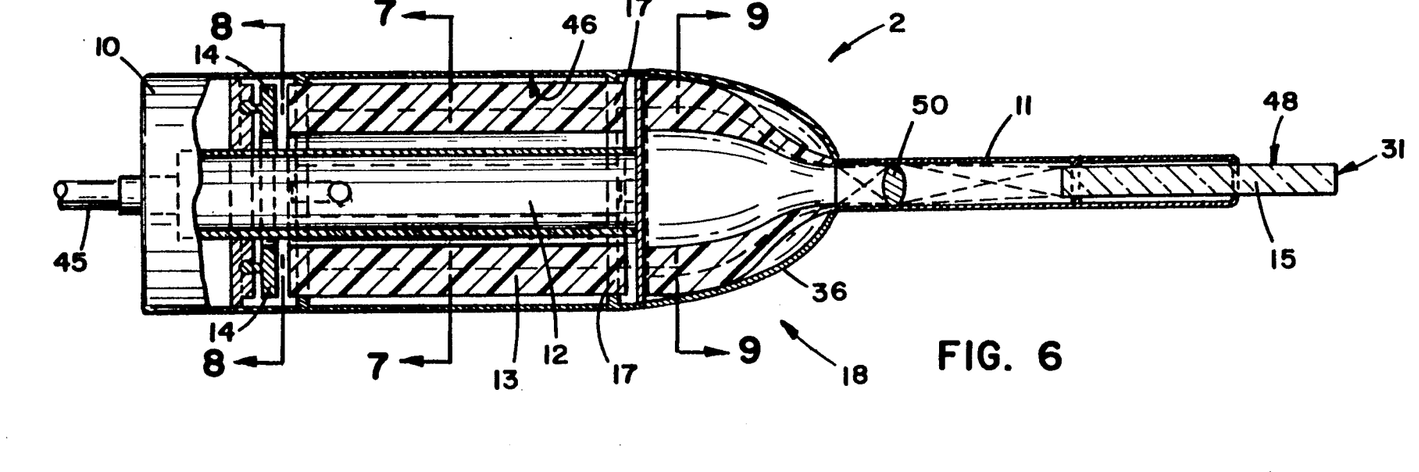
FIG. 6 is a side elevational view, in section, of the third embodiment of the device of the present invention.

The foregoing description of the light horn transmission means 18 for the first embodiment is similar to the bent horn transmission means 18 for the third embodiment, illustrated in FIG. 6. For the third embodiment, however, rather than having a straight conical light horn 37, there is a lens 50 which receives the laser energy from the bent light horns 36 of the third embodiment and which directs the laser energy to the proximal end of the extension cylinder 15. Preferably, the lens 50 is made of calcium floride.

Figure 5:
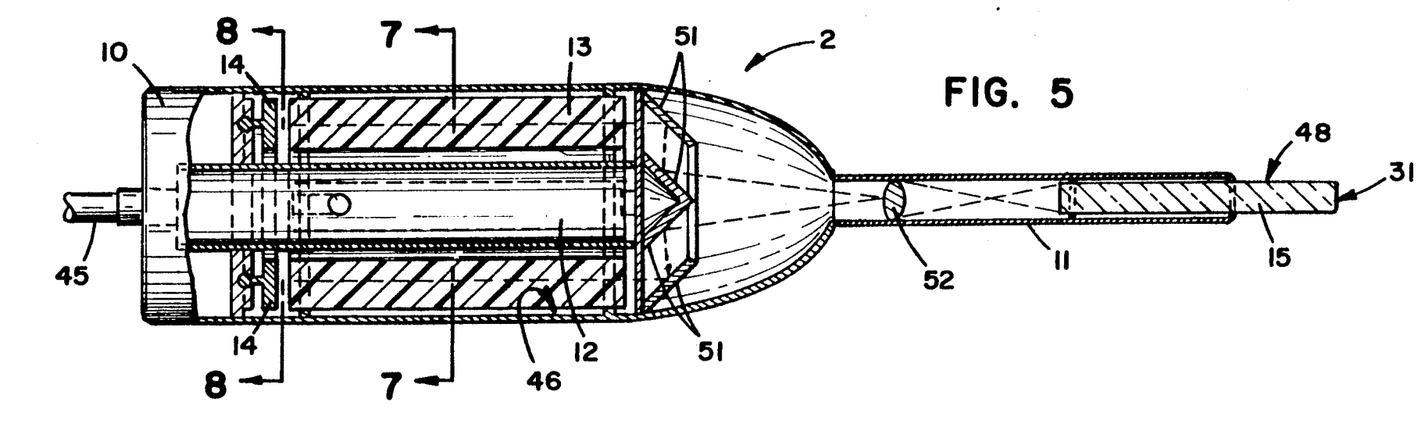
FIG. 5 is a side elevational view, in section, of the second embodiment of the device of the present invention.

The second embodiment of the medical device 2 is illustrated in FIG. 5. The probe extension 11 of this embodiment is cylindrical in shape throughout its length, rather than being tapered. In this embodiment, the laser light from the light rods 13 is captured and transmitted by a plurality of suitable mirrors 51. The mirrors cause the light beams to converge toward a single lens 52 in the proximal end of the probe extension 11. The laser light is then directed from the lens 50 to the end of the cylinder 15. The mirror arrangement is sized and configured so as to accomplish the parallel offset of the light rays which was accomplished by the bent light horn arrangement 18 in the first and third embodiments.

Figure 10:
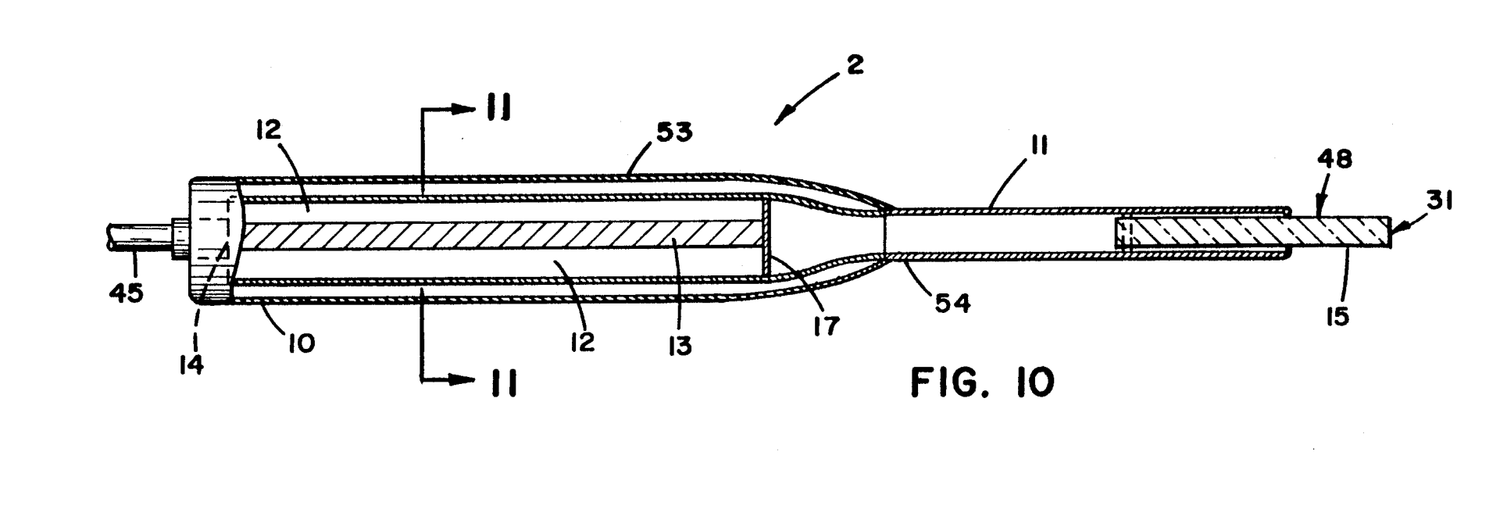
FIG. 10 is a side elevational view, in section, of the fourth embodiment of the device of the present invention.
Figure 11:
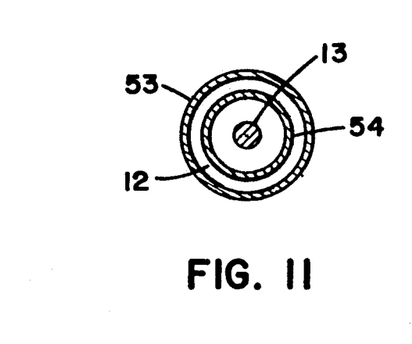
FIG. 11 is a cross-sectional view, taken along line 11—11 of FIG. 10, of the fourth embodiment of the device of the present invention.

The fourth embodiment of the present invention is illustrated in FIGS. 10-11. In the fourth embodiment, the hand piece portion 10 is a cylindrical glass tube 53. The tube 53 contains a central laser rod 13 having a mirror 14, 19 at its ends. This embodiment also preferably utilizes an erbium YAG laser. In the fourth embodiment, the laser pump energy emanates from a flashtube 12, which is a cavity or annulus formed by the cylindrical walls 53, 54. The flashtube 12 is filled with a high-pressure noble gas having suitable electrodes, e.g., Xenon. In this embodiment, the cylinder 15 is directly in line with the laser rod 13, and the laser light is emitted in a straight line from the rod 13 to the proximal end of the cylinder 15.

The medical device 2 of the present invention also preferably includes an irrigation system 21. The irrigation system 21 is illustrated only in conjunction with the first embodiment shown in FIGS. 2 to 3, but is equally applicable and preferably utilized with the other embodiments as well. The probe 11 includes an irrigation port or aperture 43 which is positioned in the patient's eye. Saline solution introduced through conduit 21, chamber 41 and aperture 43 can selectively provide for flushing of the site of surgery and also replacement of lost volume due to removal of the emulsified material. At the end of surgery, probe extension 11 is readily withdrawn from the eye.

A second fluid communication system provides for withdrawal of the emulsified material from the vicinity of the probe tip 31. In the preferred embodiment, a vacuum draw applied by means of conduit 27 is used to withdraw emulsified material, through aperture or aspiration port 35 and chamber 23, outwardly from the eye.

From the above description, it will be understood that also according to the present invention a method is provided for the removal of cataracts. Generally, steps of the method comprise application of laser emulsification through the utilization of a device such as that described capable of transmitting relatively low energy laser emissions to a selected point of surgery within a patient's eye. More specifically, the preferred method involves utilization of a hand held tool having a removable and replaceable cylinder which is manipulated so as to emulsify the cataract or other surgical target. The tool 2 contains portable laser generation and transmission means within the handpiece 10. Also, preferably, the tool 2 utilized to effect the method includes means associated therewith for removal of emulsified material, and also fluid transport means for provision of saline solution or the like into the location from which the emulsified material has been removed.

It is to be understood that while certain embodiments of the present invention have been illustrated and described, the invention is not to be limited to the specific forms or arrangement of parts herein described and shown. Changes can be made in detail, especially in matters of shape, size and arrangement of parts, within the principles of the present invention, to the full extent indicated by the broad general meaning of the appended claims.

What is claimed is:

1. An apparatus for conducting laser emulsification surgery, said apparatus comprising:
   (a) a laser source within a housing for emitting laser light;
   (b) a probe extension mounted on said housing, said probe extension having a proximal end proximate said laser source and an opposite distal end; and
   (c) transmission means for transmitting light energy from said laser source to said proximal end of said probe extension, said transmission means including a plurality of light horns, each light horn having a proximal end which is proximate to said laser source, said light horns receiving laser radiation from said laser source and amplifying said radiation by converging it.

2. The apparatus for conducting laser emulsification surgery according to claim 1, wherein said laser source emits laser light having a wavelength of approximately 2.9 to 3.1 micrometers.

3. The apparatus for conducting laser emulsification surgery according to claim 2, wherein said laser light 4. The apparatus for conducting laser emulsification surgery according to claim 2, wherein said light horns have straight walls of conically tapering cross-section.

5. The apparatus for conducting laser emulsification surgery according to claim 2, wherein said light horns have curved walls of tapering cross-section.

6. The apparatus for conducting laser emulsification surgery according to claim 2, further comprising an elongate optical cylinder element removably mounted in said probe extension and retained therein by a probe extension mounting and release mechanism, said optical cylinder having a probe tip projecting outwardly from said probe extension.

7. The apparatus for conducting laser emulsification surgery according to claim 6, wherein said cylinder element is made of calcium fluoride.

8. The apparatus for conducting laser emulsification surgery according to claim 7, wherein said laser source is positioned within a source housing and includes a central longitudinal flashlamp which is surrounded by a plurality of parallel laser rods, wherein said source housing includes a reflective inner wall.

9. The apparatus for conducting laser emulsification surgery according to claim 8, wherein said rods are positioned so as to be in close proximity to said inner wall and to each other.

10. An apparatus for conducting laser emulsification surgery according to claim 6, further comprising a lens which receives light from said light hours and which converges light onto said optical cylinder element.

11. An apparatus for conducting laser emulsifications surgery according to claim 6, wherein the optical cylinder element is constructed of material selected from the group consisting of magnesium flouride, zinc sulfide, zinc selenide, magnesium oxide, and cadmium teleride.

12. The apparatus for conducting laser emulsification surgery according to claim 2, wherein said light horns have curved walls of tapering cross-section.

13. An apparatus for conducting laser emulsification surgery, said apparatus comprising:

(a) a plurality of laser rods for emitting laser light, said plurality of laser rods being positioned within a housing in a manner parallel to and surrounding a central longitudinal flashlamp, said housing having a reflective inner walls;

(b) a probe extension mounted on said housing, said probe extension having a proximal end proximate said plurality of laser rods and an opposite distal end; and (c) transmission means for transmitting light energy from each of said laser rods to said proximal end of said probe extension, said transmission means including a plurality of mirrors, said mirrors receiving laser radiation from said plurality of laser rods and amplifying said radiation by converging it; and (d) a lens which receives light from said mirrors; and (e) an optical cylinder element removably mounted in said probe extension; said lens converging light onto said optical cylinder element.

14. The apparatus for conducting laser emulsification surgery according to claim 13, wherein each of said laser rods emits laser light having a wavelength of approximately 2.9 to 3.1 micrometers.

15. The apparatus for conducting laser emulsification surgery according to claim 14, wherein each of said laser rods in an Erbium YAG laser.

16. The apparatus for conducting laser emulsification surgery according to claim 13, wherein said rods are positioned so as to be in close proximity to each other.

17. An apparatus for conducting laser emulsification surgery, said apparatus comprising:

(a) means for emitting laser light, said emitting means including a longitudinal flashlamp and a plurality of laser rods positioned within a housing, said laser light emitting means generating laser light having a wavelength of approximately 2.9–3.1 micrometers;

(b) a probe extension mounted on said housing, said probe extension having a proximal end proximate said laser light emitting means and an opposite distal end;

(c) transmission means for transmitting said light from said laser emitting means to said proximal end of said probe extension including a plurality of light horns, each light horn having a proximal end which is proximate to an end of one of said laser rods, said light horns receiving laser radiation from said laser rods and amplifying said radiation by converging it; and (d) cooling means proximate said laser rods for cooling said laser light emitting means.

18. The apparatus for conducting laser emulsification surgery according to claim 17, further comprising:

(a) a lens which receives light from said light horns; and (b) an optical cylinder element removably mounted in said probe extension; said lens converging light onto said optical cylinder element.

19. The apparatus for conducting laser emulsification surgery according to claim 17, wherein said light horns have straight walls of conically tapering cross-section.

20. The apparatus for conducting laser emulsification surgery according to claim 17, wherein said light horns have curved walls of tapering cross-section.

21. An apparatus for conducting laser emulsification surgery, said apparatus comprising:

a) light emitting means comprising a flashlamp and a plurality of parallel laser rods surround said flashlamp, said laser rods being positioned within a housing to minimize interstitial spacing between adjacent rods;

b) a probe extension mounted on said housing, said probe extension having a proximal end proximate said laser light emitting means and opposite distal end;

c) an elongate optical cylinder element constructed of calcium fluoride mounted in said probe extension, said optical cylinder element having a probe tip projecting outwardly from said probe extension; and d) transmission means for transmitting said laser light from said laser light emitting means to said proximal end of said probe extension.

22. A handheld apparatus for conducting laser emulsification and microsurgery, said apparatus, comprising:

(a) handheld means for emitting laser light comprising a housing containing a plurality of laser rods surrounding a longitudinal flashlamp;

(b) a solid inflexible probe extension with a first end proximate said laser rods and a second end constructed and arranged for operative use at emulsification and surgical sites; and (c) coupling means for coupling said laser light emanating from said laser rods into said probe extension, whereby said laser light is transmitted to said emulsification and surgical site.

23. A handheld apparatus for conducting laser surgery, said apparatus comprising:

(a) means for emitting laser light comprising a plurality of Erbium YAG laser rods positioned around and parallel to a flashlamp, said flashlamp and said laser rods being located in a common housing suitable for manipulation by a surgeon's hand independent of any other support;

(b) a probe extension mounted on said housing, said probe extension having a proximal end proximate said means for emitting laser light and an opposite distal end; and (c) transmission means for transmitting said laser light from said laser rods to said proximal end of said probe extension.

24. A handheld apparatus for conducting laser emulsification surgery, comprising:

(a) means for emitting laser light comprising a flashlamp and a laser rod each positioned with a common housing, said common housing comprising an ergonomically constructed housing suitable for manipulation and use by a user's hand independent of any other support structure;

(b) a probe extension mounted on said housing, said probe extension having a proximal end proximate said means for emitting laser light and an opposite distal end, said probe extension comprising an extension cylinder probe constructed of solid material; and (d) transmission means for transmitting said laser light from said laser rod to said proximal end of said probe extension whereby said laser light is then transmitted to a laser emulsification surgical site.

25. A handheld apparatus for conducting laser emulsification surgery according to claim 24 wherein said extension cylinder probe comprises solid material selected from the group consisting of calcium fluoride, magnesium fluoride, zinc sulfide, zinc selenide, magnesium oxide, and cadmium teleride.

26. A handheld apparatus for conducting laser emulsification surgery, comprising:

(a) means for emitting laser light comprising a flashlamp and a laser rod each positioned within a common housing, said common housing comprising an ergonomically constructed housing suitable for manipulation and use by a user's hand independent of any other support structure;

(b) a probe extension mounted on said housing, said probe extension having a proximal end proximate said means for emitting laser light and an opposite distal end, said probe extension comprising:
  (i) an extension cylinder probe constructed of solid material; and
  (ii) a mounting and release mechanism for mounting said extension cylinder probe in said probe extension and for selectively and readily releasing said extension cylinder probe to facilitate sterilization; and (c) transmission means for transmitting said laser light from said laser rod to said proximal end of said probe extension whereby said laser light is then transmitted to a laser emulsification surgical site.

27. A handheld apparatus for conducting laser emulsification surgery, comprising:

(a) means for emitting laser light comprising a central longitudinal flashlamp and a plurality of laser rods positioned parallel to said flashlamp, said flashlamp and said laser rods being located within a housing comprising a reflective inner wall, said laser rods being positioned in close proximity to said reflective inner wall and to adjacent rods, said housing being constructed and arranged for operative support and surgical manipulation by a user's hand independent of any other support;

(b) a probe extension mounted on said housing, said probe extension having a proximal end proximate said means for emitting laser light and an opposite distal end; and (c) transmission means for transmitting said laser light from said laser rods to said proximal end of said probe extension.

* * * * *

UNITED STATES PATENT AND TRADEMARK OFFICE
CERTIFICATE OF CORRECTION

PATENT NO. : 5,074,861
DATED : December 24, 1991
INVENTOR(S) : Schneider et al.

It is certified that error appears in the above-indentified patent and that said Letters Patent is hereby corrected as shown below:

Column 1, line 5, "07/797,699" should read --07/197,699--.

Column 2, line 28, delete "the" after the word "a".

Column 4, line 26, delete "a" after the word "that".

Column 8, line 68, "floride" should read --fluoride--.

Claim 3, Column 10, line 28, insert --source is an Erbium Yag laser.-- after the word "light".

Claim 13, Column 11, line 5, "walls" should read --wall--.

Claim 11, Column 10, line 62, "flouride" should read --fluoride--.

Claim 21, Column 11, line 67, "surround" should read --surrounding--.

Signed and Sealed this

Twenty-eight Day of February, 1995

Attest:

BRUCE LEHMAN

Attesting Officer

Commissioner of Patents and Trademarks